United States Patent [19]

Gordon

[11] Patent Number: 4,673,386

[45] Date of Patent: Jun. 16, 1987

[54] BLOOD SAMPLER DEVICE

[76] Inventor: Mark G. Gordon, 13182 Woodland Dr., Tustin, Calif. 92680

[21] Appl. No.: 837,083

[22] Filed: Mar. 6, 1986

[51] Int. Cl.$^4$ .............................................. A61M 5/00
[52] U.S. Cl. ......................................... 604/48; 604/4; 604/183; 604/246; 128/765
[58] Field of Search ............................. 604/48, 80–86, 604/124–125, 181, 183, 186, 246; 128/760, 765

[56] References Cited

U.S. PATENT DOCUMENTS

| | | | |
|---|---|---|---|
| 986,263 | 3/1911 | Bevill | 604/183 |
| 4,105,500 | 8/1978 | Libman et al. | 128/765 X |
| 4,114,617 | 9/1978 | Turner et al. | 604/186 |
| 4,263,922 | 4/1981 | White | |
| 4,289,648 | 9/1981 | Hoskins et al. | |
| 4,316,473 | 2/1982 | Beskin | |
| 4,341,224 | 7/1982 | Stevens | 128/765 |
| 4,370,987 | 2/1983 | Bazell et al. | 128/765 X |
| 4,385,637 | 5/1983 | Akhavi | |
| 4,457,753 | 7/1984 | Pastrone | |
| 4,533,348 | 8/1985 | Wolfe et al. | 604/92 |

Primary Examiner—Dalton L. Truluck
Attorney, Agent, or Firm—Stetina and Brunda

[57] ABSTRACT

Method and apparatus are disclosed for drawing blood from an injection site through an arterial line connected to a fluid supply. The apparatus includes a variable capacity pump mechanism housing having inner walls defining an interior chamber. The housing includes first and second ports connected to a variable capacity interior chamber. A retractable piston is disposed within the housing and is adapted to traverse within the chamber. A piston sealing member is provided about the piston in slidable sealing engagement with the chamber walls to cause fluid to be drawn into the chamber, thereby facilitating the extraction of a blood sample along the arterial line without the need to discharge an initial sample containing disproportionate amounts of supply fluid.

14 Claims, 6 Drawing Figures

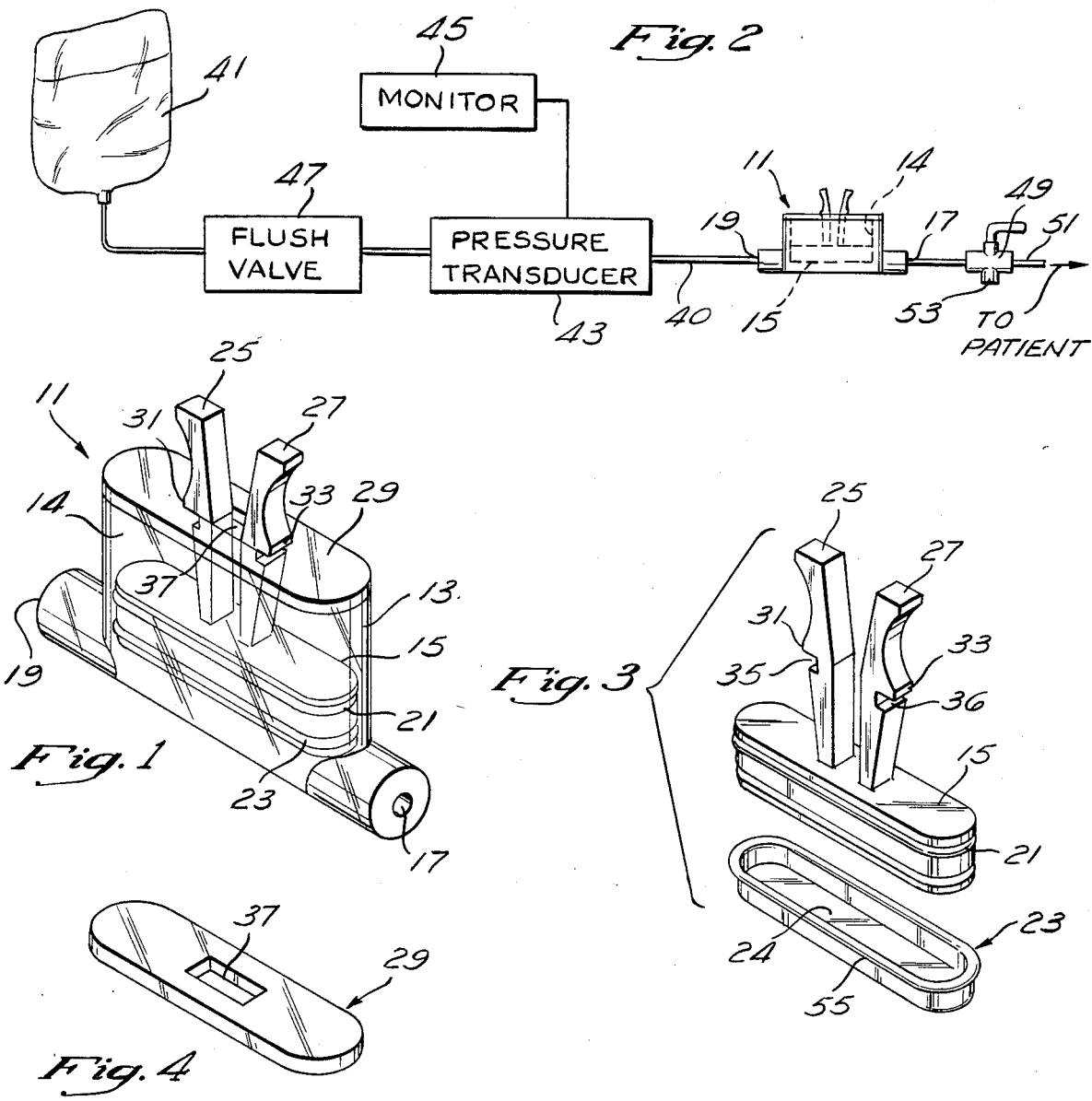
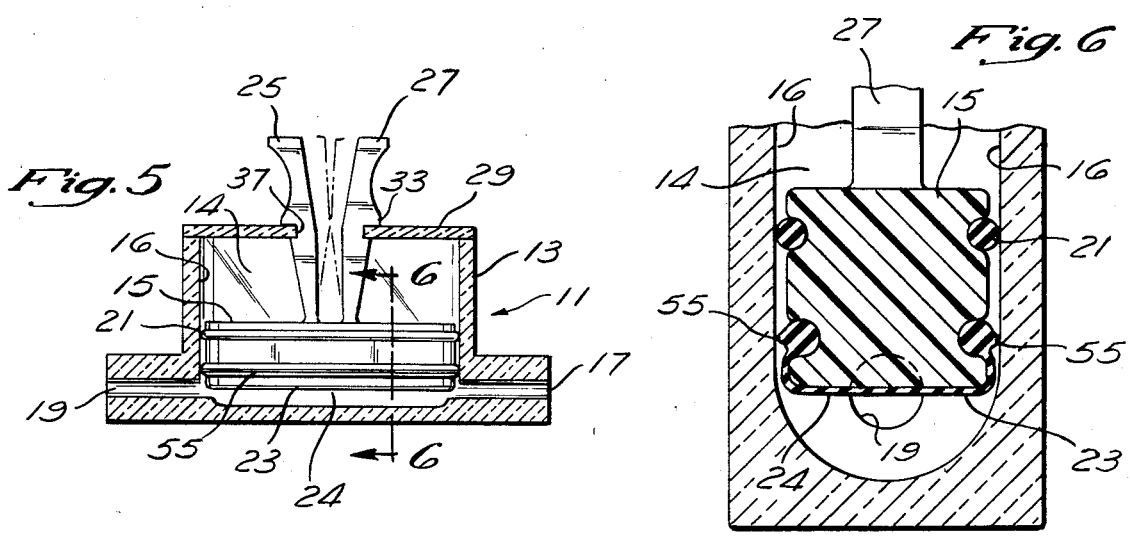

BLOOD SAMPLER DEVICE

BACKGROUND OF THE INVENTION

The present invention relates to mechanisms useful in drawing blood from an arterial pressure monitoring line. More particularly, the invention relates to a pump storage mechanism adapted to reverse the flow and temporarily store fluid in an arterial line to facilitate drawing uncontaminated blood through the arterial line.

Arterial and venous infusion lines are used to inject fluids into patient's bloodstream. Various types of devices have long been used to regulate the flow of fluid from a supply container to the injection site. As is well known to health care practitioners, the flow of fluid from the supply can be turned off and blood allowed to flow in the reverse direction through the arterial line to facilitate taking periodic blood samples. The frequency of such blood samples may vary in accordance with the nature of the patient's illness and other factors. In some cases, blood may need to be drawn on a daily or hourly basis. Where the frequency of such sampling is greater, the need to safely and efficiently draw blood, without waste, becomes greater. In certain cases, such as in the case in neo-nates, which have a more limited blood supply than adults, the need to avoid unnecessary discharging of blood is particularly significant.

Contemporary mechanisms for drawing blood from an arterial line utilize a plurality of stopcock mechanisms that preclude the flow of fluid from the fluid supply and allow blood to flow from the patient into a collecting syringe connected to a removal port formed in one of the stopcocks. Such mechanisms typically require that the person drawing the blood remove two samples from the removal site in the arterial line. The first sample, generally approximately 5 milliliters in volume, potentially includes the supply fluid in the arterial line downstream of the removal port. Thus, that sample must be discarded before a representative blood sample is obtained at the removal port. In order to insure that all of the supply fluid is removed from the line between the removal site and the patient, enough fluid is typically removed such that some of the patient's blood is also discharged in the process. After the initial sample has been discharged, the second sample is typically obtained which includes the blood to be tested.

Aside from the unnecessary loss of blood, the contemporary two sample process potentially introduces other undesirable effects relating to such problems as the potential introduction of air into the arterial line and potential introduction of contaminants into the blood supply. The two step process also requires substantial effort on the part of the nurses or other clinicians who must draw the blood sample.

The present invention is directed to a mechanism for eliminating the need to undertake such a two step process to withdraw blood through an arterial line. As described in more detail below, the present invention comprises a combination pump/storage mechanism which accomodates the return flow of the downstream fluid such that a single sample may be taken from the removal port, with that sample being clear of supply fluid and therefore representative of the patient's blood supply.

SUMMARY OF THE INVENTION

Method and apparatus are disclosed for drawing blood from an injection site through an arterial line connected to a fluid supply. The apparatus includes a variable capacity pump mechanism housing having inner walls defining an interior chamber. The housing includes first and second ports connected to a variable capacity interior chamber. A retractable piston is disposed within the housing is adapted to traverse within the chamber. A piston sealing member is provided about the piston in slidable sealing engagement with the chamber walls to cause fluid to be drawn into the chamber, thereby facilitating the extraction of a blood sample along the arterial line without the need to discharge an initial sample containing disproportionate amounts of supply fluid. The pump sealing member is further provided with a rigid lower surface to permit contact with the fluid within the chamber without attenuating the pressure of that fluid.

Piston retraction members are attached to the piston to facilitate movement of the piston within the chamber. The piston retraction members may be formed as flexures having integral stops and recesses to regulate the movement of the piston within the chamber.

BRIEF DESCRIPTION OF THE DRAWINGS

FIG. 1 is a perspective drawing of one embodiment of the present invention.

FIG. 2 is a block diagram illustrating use of the present invention in an arterial line.

FIG. 3 is an exploded perspective drawing of a portion of the mechanism illustrated at FIG. 1.

FIG. 4 is a perspective drawing of a portion of the mechanism illustrated at FIG. 1.

FIG. 5 is a front sectional view of the mechanism illustrated at FIG. 1.

FIG. 6 is a side sectional view of a portion of the mechanism illustrated at FIG. 5.

DETAILED DESCRIPTION OF THE PRESENTLY PREFERRED EMBODIMENT

FIG. 1 illustrates the presently preferred embodiment of the invention. As more fully described below, the invention is adapted to facilitate withdrawal of blood through an arterial and/or venous infusion line by reversing the flow of the supply fluid and temporarily storing fluid residing downstream of the removal port, i.e., between the removal port and the injection site. For purposes of this invention, the terms arterial line and/or line shall be defined to include any patient cooperative blood or fluid control line. The mechanism illustrated at FIG. 1 comprises a housing 13 having interior sidewalls to define an inner, oblong shaped chamber 14. Piston 15 is formed to fit and generally traverse chamber 14. Ports 17 and 19 are each connectable to an arterial line connecting the fluid supply to the patient. Ring 21 is preferably formed as an elastomeric member disposed about the outer surface of piston 15. Ring 21 functions to guide piston 15 as it traverses within chamber 14. Sealing member 23 seals the piston against the inner surfaces of chamber 14 such that upon retraction of piston 15, i.e., lifting the piston upward, a negative pressure is created drawing a variable volume of fluid into the housing 13. Piston retraction members 25 and 27 are connected to piston 15 to facilitate the retraction of piston 15 within chamber 14. In the presently preferred embodiment, piston retraction members 25 and 27 are formed as flexures shaped to cooperate with cap 29 to guide the piston 15 and thereby prevent the piston from twisting or jamming as it traverses within chamber 14. As described in more detail below, flexures 25 and 27 are provided with notched regions and stops to further regulate the movement of attached piston 15.

FIG. 2 is a block diagram illustrating the present invention as used in an arterial line 40 connected to a patient. Fluid supply 41 may be any of a variety of fluid solutions adapted for injection into the bloodstream of a patient. Pressure transducer 43 is operative to sense the pressure within the arterial line 40. Monitor 45 is connected to pressure transducer 43 and is adapted to display the pressure reading sensed by pressure transducer 43. Flush valve 47 is adapted to regulate the flow of fluid from supply 41 to the patient. In operation, flush valve 47 is turned off when a blood sample is to be taken. Thus, retraction of piston 15 within mechanism 11 will not draw fluid from supply 41 into chamber 14. Instead, retraction of piston 15 will create a negative pressure drawing at least the supply fluid between mechanism 11 and the injection site into the chamber 14. In practice, piston 15 may be retracted sufficiently to also draw blood from the patient through valve 49 and into chamber 14 within mechanism 11.

Valve 49 is preferably adapted as a three-way valve, or the like, adapted to selectively pass fluid between port 17 and conduit 51 or between port 53 and conduit 51. When valve 49 is adjusted to enable fluid to pass between port 53 and conduit 51, a blood sample may be taken at port 53. After piston 15 has been retracted to fill chamber 14 with the fluid in conduit 51, valve 49 is turned to enable the fluid then within conduit 51, i.e., blood, to pass through valve 49 and into an attached heparinized glass syringe. Thus, any of the fluid being injected into the bloodstreamm which has entered into conduit 51 is withdrawn and stored into chamber 14 such that the fluid extracted from port 53 does not include an unrepresentative quantity of such fluid in the bloodstream.

In practice, a five mililiter heparinized glass syringe is attached to port 53 of valve 49. Syringes marketed under the trademarks LUER-TIP and LUER-LOK have been found to be satisfactory for connection to the valve and storage of the withdrawn blood. As will be recognized by those skilled in the art, other types of syringes and valves may be alternately used within the scope of the present invention.

FIG. 3 illustrates in more detail the piston 15 and related parts. As shown at FIG. 3, piston 15 is formed as a generally oblong member adapted to traverse within chamber 14. The oblong shape of piston 15 and chamber 14 permits the mechanism 11 to have a low profile for ease of attachment to the patient. The shape of piston 15 and chamber 14 also provide greater surface area facing the fluid and thereby facilitate the ease of drawing blood into chamber 14.

Sealing member 23, preferably formed of molded elasatomeric material, is disposed about piston 15 and is provided with wiper 55, shown in more detail at FIG. 6. Wiper 55 helps to prevent fluid from passing between the sealing member 23 and sidewalls 16. Sealing member 23 is further provided with a rigid lower surface 24 which directly contacts the fluid passing through the mechanism 11. The lower surface 24 is formed such that, when sealing member 23 is seated upon piston 15, the rigid surface 24 is not displaceably to attenuate or otherwise alter the pressure of fluid passing through the arterial line 40.

Piston retraction members 25 and 27 are connected to piston 15 and adapted to facilitate movement of piston 15 within chamber 14. In the presently preferred embodiment, the piston retraction members 25 and 27 are constructed as flexures, formed of molded plastic material, integral with piston 15. It is to be understood, however, that numerous other types of piston retraction members may be implemented within the scope of the present invention.

As shown in FIGS. 3 and 5, flexures 25 and 27 are provided with stops 31 and 33 and slots 35 and 36, respectively. The stops and recesses are adapted to cooperate with aperture 37 formed in cap 29, illustrated at FIGS. 4 and 5. As piston 15 traverses chamber 14, the sidewalls of flexures 25 and 27 press against the inner surface of aperture 37 of cap 29. Thus, the flexures help guide and limit the movement of the piston 15 within chamber 14. As the piston is moved to the lowest desired position, as shown at FIG. 5, stops 31 and 33, and slots 35 and 36 engage aperture 37 to hold the flexures 25 and 27 in place. Thus, the piston 15 is maintained in a fixed, rigid position to prevent attenuation of the pressure within arterial line 40 due to movement of the piston. Upon squeezing the flexures 25 and 27 together, aperture 37 may be removed from locking engagement with slots 35 and 36 thereby enabling upward motion of the piston 15. Stops 31 and 33 are preferably sized such that they will remain in abutting engagement with cap 29 even when the flexures 25 and 27 are squeezed together, thereby preventing the piston 15 from being accidentally depressed beyond the lowermost desired seating position. In addition, cap 29 provides a positive secure stop which prevents arterial pressure developed in the line from ever pushing piston 15 all the way out of chamber 14.

By proper positioning the slots 35 and 36 and stops 31 and 33 along fixtures 25 and 27, the lowermost position of piston 15 will never totally preclude fluid flowing through the mechanism 11. Good flushing is therefore possible along the lower surfaces of sealing member 23. Moreover, slots 35 and 36 and stops 31 and 33 are further located such that fluid does not contact the upper surface of sealing member 23 even when piston 15 is in the lowermost position. This arrangement limits the likelihood that fluid may become trapped along the outer surfaces of piston 15 between members 21 and 23, therefore reducing the potential for contamination in that area.

FIG. 6 illustrates a side sectional view of the mechanism illustrated at FIG. 5. FIG. 6 further illustrates the sealing and wiping action of wipers 55 against sidewalls 16. As also shown at FIG. 6, the port 19 is preferably below the level of wiper 55 to minimize the possibility of contamination, as described above. Guiding member 21 is disposed about piston 15 and traverses chamber 14 in sliding relation with the sidewalls 16, thus facilitating the motion of the piston by minimizing potential twisting or jamming within the chamber 14.

It is to be understood that the construction described and illustrated above represent only the presently preferred embodiment of the invention and that various modifications and additions may be made to that embodiment without departing from the spirit and scope of the present invention. For example, alternative types and sizes of pistons, piston engaging members, and piston sealing members may be utilized. Similarly, cap 29 may be formed integral with the housing 13 or otherwise modified to form a different aperture for operation in conjunction with different piston engaging members. Such modifications as may be obvious to one skilled in the art may be implemented to adapt the present invention for use in conjunction with a variety of different applications.

What is claimed is:

1. A temporary storage mechanism adapted to facilitate the withdrawal of blood from an injection site through an arterial line comprising:
   (a) a storage mechanism housing having inner walls defining an oblong shaped interior chamber;
   (b) a first port in fluid communication with said interior chamber, and first port being connectable to a fluid supply for introduction into a patient's bloodstream;
   (c) a second port in fluid communication with said chamber, said second port being connectable to the patient injection site;
   (d) a retractable piston disposed within said housing, said piston formed in a complementary configuration to said interior chamber and adapted to traverse said chamber; and
   (e) a piston sealing member disposed about said piston in slidable sealing engagement with said inner walls of said chamber said piston having a first fixed operative position in said chamber to prevent pressure attenuation within the arterial line and a second operative position wherein said piston is slideably retracted within said chamber to create negative pressure within said chamber, said negative pressure being effective to draw fluid into said chamber through at least one of said ports and temporarily store the same in said chamber for subsequent re-introduction into said injection site.

2. The mechanism as recited in claim 1 wherein said piston sealing member is formed as a molded elastomer sealing member having a rigid lower surface.

3. The mechanism as recited in claim 2 wherein said rigid surface is adapted for contact with fluid within said chamber without attenuating the fluid pressure therein.

4. The mechanism as recited in claim 1 further including a piston retraction member connected said piston for moving the piston within said chamber.

5. The mechanism as recited in claim 4 wherein said piston retraction member comprises a pair of flexures.

6. The mechanism as recited in claim 5 further comprising a housing cap mounted on said housing, said cap having an aperture for receiving said flexures.

7. The mechanism as recited in claim 6 wherein said flexures comprise angled elongate members connected said piston, said angled elongate members having stops along the length thereof, said stops being engageable with said cap to regulate movement of said piston within said chamber.

8. A method of drawing blood from an injection site through an arterial line connected to a fluid supply comprising:
   (a) disposing a first valve in the arterial line intermediate the fluid supply and the injection site;
   (b) disposing a variable capacity storage mechanism in the arterial line intermediate the first valve and the injection site;
   (c) disposing a second valve in the arterial line intermediate the storage mechanism and the injection site, said second valve being disposed to have a first port connected to the injection site, a second port connected to the storage mechanism and a third port connectable to a blood storage container;
   (d) disabling fluid flow through said first valve;
   (e) drawing blood downstream of the storage mechanism into the pump storage mechanism, said drawing being effective to draw blood into the arterial line through the injection site and through the second valve;
   (f) disabling fluid flow between said first and second ports of said second valve;
   (g) enabling fluid flow between said first and third ports of said second valve;
   (h) collecting a volume of blood in the blood storage container connected to said third port;
   (i) disabling fluid flow between said first and third ports of the second valve;
   (j) enabling fluid flow between said first and second ports of said second valve;
   (k) substantially discharging the fluid in the variable capacity storage mechanism into the arterial line; and
   (l) enabling fluid flow through said first valve.

9. A method of drawing blood from an injection site through an arterial line connected to a fluid supply comprising:
   (a) disposing a variable capacity storage mechanism in the arterial line intermediate the fluid supply and the injection site;
   (b) disabling fluid flow from the fluid supply to the storage mechanism;
   (c) drawing fluid in the arterial line downstream of the storage mechanism into a variable capacity chamber formed in the storage mechanism, said drawing being effective to draw blood into the arterial line intermediate the storage mechanism and the injection site;
   (d) diverting a volume of blood drawn into the arterial line into a blood storage container connected to the arterial line intermediate the injection site and the variable capacity pump storage mechanism;
   (e) discharging the fluid drawn into the variable capacity chamber back into the arterial line; and
   (f) enabling fluid flow from the fluid supply to the storage mechanism.

10. A system for drawing blood from an arterial line supplying fluid to an injection site comprising:
   (a) a fluid supply connected to the arterial line for injection into the bloodstream of a patient at an injection site;
   (b) a first valve connected to the arterial line intermediate the fluid supply and the injection site;
   (c) a variable capacity storage mechanism connected to the arterial line intermediate the first valve and the injection site, said storage mechanism comprising a variable capacity chamber in fluid communication with said fluid supply and the patient's bloodstream, said storage mechanism being effective to draw fluid in the arterial line into said variable capacity chamber;
   (d) a second valve connected to the arterial line intermediate said storage mechanism and the injection site, said second valve having a first port connected to the injection site, a second port connected to the storage mechanism, and a third port connectable to a blood storage container, said second valve further including a diverter mechanism for selectively enabling fluid flow between the injection site and one of said storage mechanism and the blood storage container.

11. The system as recited in claim 10 wherein said storage mechanism comprises:
   (a) a housing having inner walls defining an interior chamber;
   (b) a first port in fluid communication with said interior chamber, said first port being connected to said first valve;
   (c) a second port in fluid communication with said chamber, said second port being connected to said second valve;
   (d) a retractable piston disposed within said housing and adapted to traverse within said chamber;
   (e) a piston sealing member disposed about said piston in slidable sealing engagement with said inner walls for creating negative pressure within said chamber upon retraction of said piston within said chamber, said negative pressure being effective to draw fluid into said chamber through at least one of said ports.

12. The mechanism as recited in claim 10 further including a piston retraction member connected to said piston for moving said piston within said chamber.

13. The mechanism as recited in claim 11 wherein said piston retraction member comprises stops for limiting the movement of said piston.

14. The system as recited in claim 12 wherein said stops are formed to preclude said piston from moving to a position that would totally occlude fluid flow through the storage mechanism.

* * * * *